(12) United States Patent
Lapidus

(10) Patent No.: US 6,818,204 B2
(45) Date of Patent: Nov. 16, 2004

(54) STABLE FOAM FOR USE IN DISPOSABLE WIPE

(75) Inventor: Herbert Lapidus, Ridgefield, CT (US)

(73) Assignee: Combe Incorporated, White Plains, NY (US)

( * ) Notice: Subject to any disclaimer, the term of this patent is extended or adjusted under 35 U.S.C. 154(b) by 0 days.

(21) Appl. No.: 09/884,062

(22) Filed: Jun. 20, 2001

(65) Prior Publication Data

US 2002/0034455 A1 Mar. 21, 2002

Related U.S. Application Data

(60) Provisional application No. 60/213,584, filed on Jun. 23, 2000.

(51) Int. Cl.$^7$ .............................. A61K 6/00; A61K 7/00; A61K 9/00; A01N 25/02; A61L 9/04
(52) U.S. Cl. ....................... 424/43; 424/401; 424/78.03; 514/945; 514/882; 510/130
(58) Field of Search ........................... 424/1.13, 40, 43, 424/443, 47; 510/130; 514/945, 882; 428/288

(56) References Cited

U.S. PATENT DOCUMENTS

| | | | | |
|---|---|---|---|---|
| 5,141,803 A | * | 8/1992 | Pregozen | 428/288 |
| 5,431,906 A | * | 7/1995 | Mohseni et al. | 424/73 |
| 5,635,469 A | | 6/1997 | Fowler et al. | 510/406 |
| 5,837,661 A | * | 11/1998 | Evans et al. | 510/122 |
| 5,858,371 A | * | 1/1999 | Singh et al. | 424/195.1 |
| 6,015,763 A | | 1/2000 | Vlasbom | 442/123 |
| 6,030,931 A | * | 2/2000 | Vinski et al. | 510/130 |
| 6,232,496 B1 | * | 5/2001 | Carr et al. | 562/564 |
| 6,283,336 B1 | * | 9/2001 | Dwyer et al. | 222/190 |

FOREIGN PATENT DOCUMENTS

| | | |
|---|---|---|
| EP | 1 055 425 | 11/2000 |
| WO | 91/17237 | 11/1991 |
| WO | 00/66455 | 11/2000 |

OTHER PUBLICATIONS

Wenninger et al. Int'l Cosmetic Ingredient Dictionary and Handbook, 7$^{th}$ Ed., 1997, vol. 2. pp. 1693, 1695.*
Patent Abstracts of Japan, vol. 1999, No. 03, Mar. 31, 1999 (corresponds to JP 10–330799).

* cited by examiner

Primary Examiner—Sreeni Padmanabhan
Assistant Examiner—Lauren Q Wells
(74) Attorney, Agent, or Firm—Fitzpatrick, Cella, Harper & Scinto

(57) ABSTRACT

An aqueous stable foam, suitable for use as a vaginal or hemorrhoidal wipe agent, containing at least one surfactant and at least one foam stabilizing agent can be dispensed to bathroom tissue or the like for application to the vaginal or anal area.

25 Claims, 1 Drawing Sheet

STABLE FOAM FOR USE IN DISPOSABLE WIPE

This application claims the benefit of U.S. Provisional Patent Application No. 60/213,584, filed Jun. 23, 2000.

BACKGROUND OF THE INVENTION

1. Field of the Invention

The present invention relates generally to a disposable vaginal or hemorrhoidal wipe product. In particular, the present invention relates to an aqueous stable foam containing a surfactant which can be dispensed to bathroom tissue or the like for application to the vaginal or anal area.

2. Background

Conventional vaginal or hemorrhoidal wipe products are typically in the form of pre-wetted, non-flushable cloths or pads. Because these products are pre-wetted with a volatile wiping agent, it is necessary to package and store these products in sealed containers, jars, foil packets or the like in order to maintain moisture by reducing evaporation of the wiping agent. For example, Tucks brand hemorrhoidal wipes are typically stored in a screw-top jar. Due to the nature of conventional vaginal and/or hemorrhoidal wipe products and their storage requisites, a number of problems arise.

First, containers, jars, foil packets and the like, which are capable of storing a volatile wiping agent such as isopropyl alcohol, witch hazel, water or perfume, useful as a vaginal and/or hemorrhoidal wipe, are expensive. Second, there is no precise control over the amount of wiping agent dispensed with each pre-wetted cloth or pad, thereby leading to waste of the wiping agent. Third, the pre-wetted cloths or pads are not readily disposable, i.e., they are not biodegradable and can not or should not be flushed in a toilet. Fourth, the need for bulky storage containers, jars, foil packets and the like precludes portability of vaginal and/or hemorrhoidal wipe products and/or hinders their disposal. Finally, wipe products that are stored in conventional jars or dispensing wipe packets typically dry out before all of the wipes are used.

Hence, it is clear that there is a need for a readily disposable vaginal and/or hemorrhoidal wipe product which addresses the above-described problems.

SUMMARY OF THE INVENTION

The present invention is directed to a propellant-free foamable aqueous composition capable of forming a stable foam suitable for use as a vaginal or hemorrhoidal wipe agent comprising (a) water; (b) at least one surfactant; and (c) at least one foam stabilizing agent.

The present invention is also directed to a system for delivering a foam suitable for use as a vaginal or hemorrhoidal wipe agent, which comprises a propellantless dispenser containing the propellant-free foamable aqueous composition according to the present invention.

The present invention is also directed to a stable foam suitable for use as a vaginal or hemorrhoidal wipe agent formed by dispensing from a propellantless dispenser the propellant-free foamable aqueous composition according to the present invention.

The present invention is also directed to a vaginal or hemorrhoidal wipe product comprising the stable foam of the present invention disposed on bathroom tissue.

Still further, the present invention includes a foam wipe kit comprising (a) a propellantless finger actuated mechanical pump dispenser containing a propellant-free foamable aqueous composition capable of forming a stable foam on dispensing; and (b) a disposable substrate, such as bathroom tissue, for receiving the stable foam.

DETAILED DESCRIPTION

Figure 1:
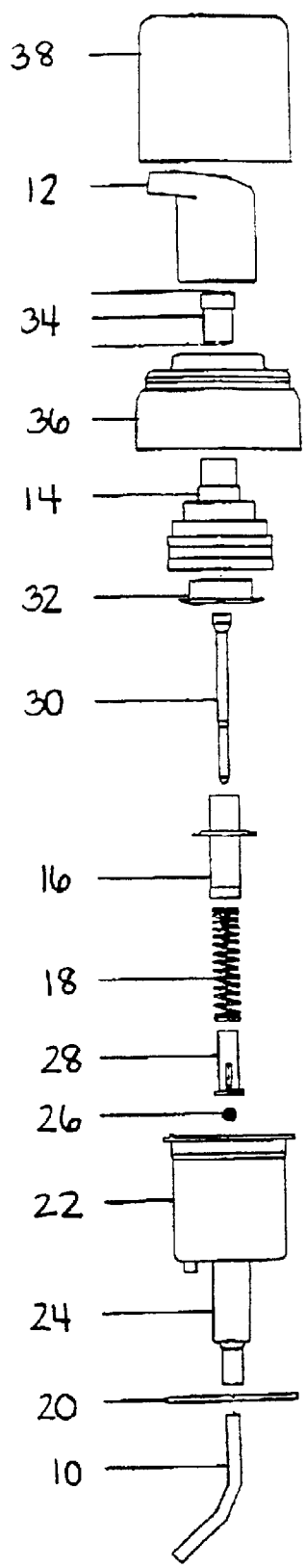
FIG. 1 is a schematic diagram of the F2 Finger Pump Foamer™ suitable for use in the present invention.

The present invention is directed to a readily disposable vaginal or hemorrhoidal wipe product. As used herein, the terms "wipe product" and "wiping agent" are used interchangeably with "cleansing product" and "cleansing agent". In particular, the present invention relates to an aqueous stable foam containing at least one surfactant and at least one foam stabilizing agent which can be dispensed to bathroom tissue or the like for application to the vaginal or perineal area.

One of the advantages of such a foam is that a disposable vaginal or hemorrhoidal wipe product is achieved without the use of a foil packet, a Tucks brand jar or a diaper wipe container. Advantageously, a desired amount of foam may be applied and removed using several pieces of bathroom tissue, which is readily available, biodegradable and easily flushed. As employed herein, bathroom tissue includes toilet paper or any other natural or synthetic product, such as Kleenex brand tissue, generally present in bathrooms or rest areas for sanitary or other purposes.

The foam of the present invention is stable. For purposes of this invention, a stable foam may be generally defined as a non-irritating dry, relatively firm foam with low solids content which forms foam bubbles with a low contact angle with bathroom tissue and which maintains the integrity of the bathroom tissue. A relatively low concentration of skin-compatible surfactants and water soluble foam stabilizers present in the wipe agent of the present invention produces a high void-containing or light density foam which barely, if at all, wets the bathroom tissue so that the tissue maintains its integrity during application of the wipe agent composition to the anal and/or vaginal mucosal surfaces.

In other words, the foam remains for an extended period of time, unless and until applied onto a surface with pressure such as by rubbing and/or with increasing temperature. The pressure and/or increased temperature causes the foam to collapse, thus making the wipe agent(s) available to clean and/or medicate the tissues so treated. As a result, the present foam can be applied to bathroom tissue or like substrate, without being absorbed by such. The foam-carrying substrate can then be applied to the vaginal or anal area.

In one embodiment, the present invention is directed to a propellant-free foamable aqueous composition capable of forming a stable foam suitable for use as a vaginal or hemorrhoidal wipe agent. This aqueous composition is charged into a propellantless foam dispenser to form the foam of the present invention for use in a vaginal or hemorrhoidal wipe product.

The propellant-free foamable aqueous composition of the present invention comprises water, at least one surfactant and at least one foam stabilizing agent.

Water, preferably deionized water, is typically present in the propellant-free foamable aqueous composition in an amount from about 70% to about 98% by weight, preferably from about 80% to about 98% by weight, and most preferably about 90% by weight. Unless otherwise indicated, all ingredient weight % are based on the total weight of the propellant-free foamable aqueous composition.

In general, in order to provide an enhanced stable foam according to the present invention, water-soluble compounds are preferably employed. Such compounds are storage stable and readily dispensed by a propellantless mechanical pump.

Any type of compatible surfactant, e.g., nonionic, anionic, amphoteric, suitable for use in human hygienic products is suitable for use in the present invention. The surfactant should be capable of forming a foam when mixed with air in a finger actuated, mechanical pump foamer. Such surfactants include, without limitation, those which do not irritate mucous membranes such as polyethylene 20 cetyl ether (Brij 58)™, a nonionic surfactant; sodium lauroyl sarcosinate (Hamposyl L-30)™, sodium lauryl sulfoacetate (Lathanol LAL)™ and sodium laureth sulfate (Sipon ESY)™— anionic surfactants; lauramidopropyl betaine (Monateric LMAB)™, an amphoteric surfactant, as well as polysorbate 20, TEA-cocoyl glutamate, disodium cocoamphodiacetate and combinations thereof. Typically, the surfactant is present in the instant invention in an amount from about 2% to about 35% by weight, and preferably from about 5% to about 15% by weight.

According to a preferred embodiment of the present invention, a blend of Tween 20, Amisoft CT-12 and Monateric CDX 38 Mod. (polysorbate 20, TEA-cocoyl glutamate, disodium cocoamphodiacetate, respectively) is employed. In this embodiment, Tween 20 is present in an amount ranging from about 0.1% to about 2%, preferably about 1%; Amisoft is present in an amount ranging from about 1% to about 15%, preferably about 5%; and Monateric is present in an amount ranging from about 1% to about 15%, preferably about 5%.

At least one foam stabilizing agent is also present in the foamable aqueous composition of the present invention. Suitable foam stabilizing agents include, without limitation, natural or synthetic gums such as xanthan gum, polyalkylene glycols such as polyethylene glycol, alkylene polyols such as glycerine and propylene glycol and combinations thereof. Typically, the foam stabilizers are present in an amount from about 0.10% to about 5%, preferably about 2% to about 4%.

In general, alkylene polyols are typically employed in amounts from about 0.1% to about 10%, preferably from about 3% to about 5%; gums are employed in amounts ranging from about 0.05% to about 1%, preferably from about 0.05% to about 0.15%; and/or polyalkylene glycols are present in amounts ranging from about 0.05% to about 2%.

Preservatives may also be present in the foamable aqueous composition of the present invention. Suitable preservatives include, without limitation, methylparaben, propylparaben, Glydant Plus (DMDM hydantoin and iodopropynyl butylcarbamate) and combinations thereof. Typically, preservatives are present in an amount from about 0.10% to about 1%, preferably from about 0.40% to about 0.60%, and most preferably about 0.50%.

In certain embodiments of the present invention, namely the foamable aqueous composition suitable for use in a hemorrhoidal wipe product, water soluble medicaments may also be present. Suitable medicaments include, without limitation, pramoxine HCl, phenylephrine HCl, ephedrine sulfate, dibucaine HCl and combinations thereof. Typically, such medicaments are present in conventional amounts.

Other constituents normally found in vaginal or hemorrhoidal wipe products may be present in the foamable aqueous composition of the present invention, if desired. Such constituents typically include, but are not limited to, lubricants such as Cetiol HE (PEG-7 glyceryl cocoate), chelating agents such as disodium EDTA, moisturizers such as aloe powder, healing agents such as vitamin E acetate (tocopherol acetate), fragrance, color and mixtures thereof.

One of ordinary skill in the art would readily appreciate that a particular ingredient may serve more than one function in the foamable aqueous composition of the present invention. For example, disodium cocoamphodiacetate functions not only as a surfactant but also as a foam stabilizer.

Another embodiment of the present invention is a system for delivering a foam suitable for use in a vaginal or hemorrhoidal wipe product comprising a propellantless dispenser containing a propellant-free foamable aqueous composition of the invention. Yet another embodiment of the present invention is a stable foam formed by dispensing from a propellantless dispenser a propellant-free foamable aqueous composition as described above.

According to the present invention, the stable foam of the present invention is produced using a propellantless mechanical pump. Such a pump precisely mixes water and air upon actuation to produce foam. While it may be possible to use a conventional mechanical foam dispenser, such as a squeeze foamer, best results have been achieved with a mousse-type foam dispensing finger actuated dispenser.

Preferably, the foam is produced using the F2 Finger Pump Foamer™ manufactured by AirSpray International Inc. of Pompano Beach, Fla. Such a spring-loaded valve system operates without the use of gas propellants or the like. Upon actuation, precise amounts of air and liquid are mixed, and a foam capable of maintaining its structure for a substantial length of time is dispensed. In addition, the dispenser can deliver a variable amount of foam, thereby reducing waste of the wipe agent contained therein.

The F2 Finger Pump Foamer™ is similar in design and operation to conventional propellantless finger actuated mechanical pump foamers, such as those described in U.S. Pat. No. 5,443,569, issued on Aug. 22, 1995, and U.S. Pat. No. 5,813,576, issued Sep. 29, 1998, the disclosures of which are incorporated by reference herein. Such propellantless finger actuated mechanical foamers can be employed to dispense the stable foam of the present invention.

A schematic diagram of the F2 Finger Pump Foamer™ is provided in FIG. 1 in which a dip tube 10 receives the foamable aqueous composition contained in a container body (not shown). A pump head 12 moves up and down to dispense the foam. An air piston 14 and liquid piston 16 are concentrically arranged and are urged upwardly by spring 18. A gasket seal 20, air cylinder 22, liquid cylinder 24, ball 26, plug 28, inner rod 30, and valve 32 are arranged as shown in FIG. 1 and operate generally in accordance with the corresponding elements of FIG. 1 of U.S. Pat. No. 5,443,569, incorporated by reference, and especially described in columns 12–14, thereof. In general, as the air piston and liquid piston are moved down upon actuation, the air and liquid-containing chambers are pressurized. Pressurized foamable liquid in the liquid chamber and pressurized air are mixed to produce the foam, which is homogenized into a finer foam by mesh and net members 34 after which the foam is dispensed from the nozzle tip. A basecap 36 is attached to the external cylinder just below the nozzle and an overcap 38 protects the nozzle.

The F2 Finger Pump Foamer™ is an easy-to-use dispenser, with excellent performance, and provides clean, single stroke action, zero-VOC formulations and high foam quality. Shaking the container will not affect foam quality. Precise dosage per stroke is possible, and the container is refillable.

A Synbio Dual Chambered Dispenser™ may also be utilized as the propellantless dispenser.

The aerosol type foam dispenser which employs gas propellant is inconvenient to use and produces an unsatisfactory foam compared to that produced by the present invention. Further, once the propellant volatilizes, the foam produced using an aerosol type foam dispenser collapses.

A further embodiment of the present invention is directed to a foam wipe kit. The foam wipe kit comprises (a) a propellantless finger actuated mechanical pump dispenser containing a propellant-free foamable aqueous composition capable of forming a stable foam on dispensing; and (b) a disposable substrate, such as bathroom tissue, for receiving the stable foam.

The following non-limiting examples further illustrate the present invention.

EXAMPLE 1

A foamable aqueous composition and a foam were prepared by combining the ingredients listed in Table 1 according to the below-described method.

TABLE 1

| Ingredient | Weight % |
|---|---|
| polysorbate 20 (100% active)[1] | 1.00 |
| TEA-cocoyl glutamate (30% active)[2] | 5.00 |
| disodium cocoamphodiacetate (38% active)[3] | 5.00 |
| propylene glycol | 3.00 |
| xanthan gum[4] | 0.10 |
| triclosan | 0.25 |
| perfume | 0.10 |
| DMDM hydantoin and iodopropynyl butylcarbamate[5] | 0.25 |
| deionized water | 85.24 |
| vitamin E acetate (tocopherol acetate) | 0.05 |
| aloe powder | 0.01 |

[1]sold as Tween 20 ™ by ICI Surfactants
[2]sold as Amisoft CT-12 ™ by Ajinomoto
[3]sold as Monateric CDX ™ 38 Mod. by Mona
[4]sold as Xantural 180 ™ by Monsanto
[5]sold as Glydant Plus ™ by Lonza Triclosan was added to propylene glycol in a small container using a propeller mixer. The mixture was mixed and heated slightly until all solids dissolved. Xanthan gum was mixed with deionized water in a large container using a propeller mixer. Aloe powder was added to the aqueous composition with mixing. Polysorbate 20, TEA-cocoyl glutamate, disodium cocoamphodiacetate, vitamin E acetate and DMDM hydantoin and iodopropynyl butylcarbamate were added to the aqueous mixture with mixing. The contents of both the small and the large container were combined and mixed. Perfume was added to the mixture. A cloudy yellow liquid was obtained.

The cloudy yellow liquid was charged to an AirSpray F2 Finger Pump Foamer™ and, upon discharge therefrom, formed a white stable foam. The foam was relatively firm and did not wet bathroom tissue when dispensed thereon. When applied to vaginal areas, the foam broke and was readily applied to the area indicated. Accordingly, the composition was useful as a vaginal wipe.

EXAMPLE 2

A foamable aqueous composition and a foam were prepared by combining the ingredients listed in Table 2 according to the below-described method.

TABLE 2

| ingredient | weight % |
|---|---|
| polysorbate 20 (100% active)[1] | 1.30 |
| TEA-cocoyl glutamate (30% active)[2] | 5.00 |
| disodium cocoamphodiacetate (38% active)[3] | 5.00 |
| glycerine | 3.00 |
| xanthan gum[4] | 0.10 |
| Polyethylene glycol (23 oxyethylene) | 0.20 |
| pramoxine HCl | 1.00 |
| phenylephrine HCl | 0.25 |
| methylparapen | 0.25 |
| propylparaben | 0.15 |
| disodium EDTA | 0.10 |
| PEG-7 glyceryl cocoate[6] | 0.50 |
| water, deionized | 83.15 |

[1]sold as Tween 20 ™ by ICI Surfactants
[2]sold as Amisoft CT-12 ™ by Ajinomoto
[3]sold as Monateric CDX 38 Mod. ™ by Mona
[4]sold as Xantural 180 ™ by Monsanto
[5]PEG-23M sold as Polyox WSR-12K ™ by Amerchol
[6]sold as Cetiol HE ™ by Henkel PEG-23M and water were mixed until clear. Xanthan gum was added and mixed until a uniform solution was obtained. Disodium EDTA was added and dissolved. In a separate small container, methylparaben, propylparaben, and glycerin were mixed until clear, using low heat to dissolve the parabens. Polysorbate 20, TEA-cocoyl glutamate, disodium cocoamphodiacetate were added to the aqueous mixture and mixed well. The pramoxine HCl and the phenylephrine HCl were added to the aqueous mixture and mixed until clear. The paraben mixture and the PEG-7 glyceryl cocoate were added to the aqueous mixture and mixed well. A liquid was obtained.

The liquid was charged to an AirSpray F2 Finger Pump Foamer™ and, upon discharge therefrom, formed a white stable foam. The foam was relatively firm and did not wet bathroom tissue when dispensed thereon. When applied to anal areas, the foam broke and was readily applied to the area indicated. Accordingly, the composition was useful as a hemorrhoidal wipe. When other compatible surfactants of the invention are substituted for the surfactant blends illustrated in the Examples, similar results are obtained.

While the invention has been described in terms of preferred embodiments and specific examples, those skilled in the art will recognize through routine experimentation that various changes and modifications can be made without departing from the spirit and scope of the invention. Thus, the invention should be understood as not being limited by the foregoing detailed description, but as being defined by the appended claims and their equivalents.

What is claimed is:

1. A propellant-free foamable aqueous composition consisting essentially of:

(a) water in an amount from about 70% to about 98% by weight, based on the total weight of the aqueous composition;

(b) surfactant in an amount from about 2% to about 35% by weight, based on the total weight of the aqueous composition, wherein the surfactant is a combination of polysorbate 20, triethanolamine-cocoyl glutamate and disodium cocoamphodiacetate; and (c) foam stabilizing agent in an amount from about 0.10% to about 5% by weight, based on the total weight of the aqueous composition, wherein the foam stabilizing agent is selected from the group consisting of natural and synthetic gums, polyalkylene glycols, alkylene polyols and combinations thereof;

wherein the propellant-free foamable aqueous composition is capable of forming a stable foam when dispensed from a propellantless finger actuated mechanical pump dispenser, wherein the stable foam maintains the integrity of a disposable substrate to which it is applied and wherein the stable foam is suitable for application to the vaginal or anal area.

2. The propellant-free foamable aqueous composition according to claim 1, wherein water is present in an amount from about 80% to about 98% by weight, based on the total weight of the aqueous composition.

3. The propellant-free foamable aqueous composition according to claim 2, wherein water is present in an amount of about 90%, based on the total weight of the aqueous composition.

4. The propellant-free foamable aqueous composition according to claim 1, wherein the surfactant is present in an amount from about 5% to about 15% by weight, based on the total weight of the aqueous composition.

5. The propellant-free foamable aqueous composition according to claim 1, wherein polysorbate 20 is present in an amount from about 0.1% to about 2%, triethanolamine-cocoyl glutamate is present in an amount from about 1% to about 15%, and disodium cocoamphodiacetate is present in an amount from about 1% to about 15% by weight, based on the total weight of the aqueous composition.

6. The propellant-free foamable aqueous composition according to claim 5, wherein polysorbate 20 is present in an amount of about 1%, triethanolamine-cocoyl glutamate is present in an amount of about 5%, and disodium cocoamphodiacetate is present in an amount of about 5% by weight, based on the total weight of the aqueous composition.

7. The propellant-free foamable aqueous composition according to claim 1, wherein the foam stabilizing agent is present in an amount from about 2% to about 4% by weight, based on the total weight of the aqueous composition.

8. The propellant-free foamable aqueous composition according to claim 1, wherein the foam stabilizing agent is a combination of glycerine, xanthan gum and polyethylene glycol (23 oxyethylene).

9. The propellant-free foamable aqueous composition according to claim 1, wherein alkylene polyols are present in an amount from about 0.1% to about 10%, gums are present in an amount from about 0.05% to about 1%, and polyalkylene glycols are present in an amount from about 0.05% to about 2% by weight, based on the total weight of the aqueous composition.

10. The propellant-free foamable aqueous composition according to claim 9, wherein alkylene polyols are present in an amount from about 3% to about 5% and gums are present in an amount of about 0.05% to about 0.15% by weight, based on the total weight of the aqueous composition.

11. The propellant-free foamable aqueous composition according to claim 1 further consisting of a preservative.

12. The propellant-free foamable aqueous composition according to claim 11, wherein the preservative is selected from the group consisting of methylparaben, propylparaben, DMDM hydantoin and iodopropynyl butylcarbamate and combinations thereof.

13. The propellant-free foamable aqueous composition according to claim 11, wherein the preservative is present in an amount from about 0.10% to about 1% by weight, based on the total weight of the aqueous composition.

14. The propellant-free foamable aqueous composition according to claim 13, wherein the preservative is present in an amount from about 0.40% to about 0.60% by weight, based on the total weight of the aqueous composition.

15. A propellant-free foamable aqueous composition consisting essentially of:
(a) water in an amount from about 70% to about 98% by weight, based on the total weight of the aqueous composition;
(b) surfactant in an amount from about 2% to about 35% by weight, based on the total weight of the aqueous composition, wherein the surfactant is a combination of polysorbate 20, triethanolamine-cocoyl glutamate and disodium cocoamphodiacetate;
(c) foam stabilizing agent in an amount from about 0.10% to about 5% by weight, based on the total weight of the aqueous composition, wherein the foam stabilizing agent is selected from the group consisting of natural and synthetic gums, polyalkylene glycols, alkylene polyols and combinations thereof; and
(d) medicament;
wherein the propellant-free foamable aqueous composition is capable of forming a stable foam when dispensed from a propellantless finger actuated mechanical pump dispenser, wherein the stable foam maintains the integrity of a disposable substrate to which it is applied and wherein the stable foam is suitable for application to the vaginal or anal area.

16. The propellant-free foamable aqueous composition according to claim 15, wherein the medicament is selected from the group, consisting of pramoxine HCl phenylephrine HCl, ephedrine sulfate, dibucaine HCl and combinations thereof.

17. A propellant-free foamable aqueous composition consisting essentially of:
(a) water in an amount from about 70% to about 98% by weight, based on the total weight of the aqueous composition;
(b) surfactant in an amount from about 2% to about 35% by weight, based on the total weight of the aqueous composition, wherein the surfactant is a combination of polysorbate 20, triethanolamine-cocoyl glutamate and disodium cocoamphodiacetate;
(c) foam stabilizing agent in an amount from about 0.10% to about 5% by weight, based on the total weight of the aqueous composition, wherein the foam stabilizing agent is selected from the group consisting of natural and synthetic gums, polyalkylene glycols, alkylene polyols and combinations thereof; and
(d) a constituent selected from the group consisting of lubricants, chelating agents, moisturizers, healing agents, fragrance, color and mixtures thereof;
wherein the propellant-free foamable aqueous composition is capable of forming a stable foam when dispensed from a propellantless finger actuated mechanical pump dispenser, wherein the stable foam maintains the integrity of a disposable substrate to which it is applied and wherein the stable foam is suitable for application to the vaginal or anal area.

18. A system for delivering a foam suitable for use as a vaginal or hemorrhoidal wipe agent comprising a propellantless finger actuated mechanical pump dispenser containing a propellant-free foamable aqueous composition according to claim 1.

19. A stable foam suitable for use as a vaginal or hemorrhoidal wipe agent formed by dispensing from a propellantless finger actuated mechanical pump dispenser a propellant-free foamable aqueous composition according to claim 1.

20. A vaginal or hemorrhoidal foam wipe kit comprising:
(a) a propellantless finger actuated mechanical pump dispenser containing a propellant-free foamable aqueous composition according to claim 1 capable of forming a stable foam on dispensing; and
(b) a disposable substrate for receiving the stable foam.

21. A vaginal or hemorroidal foam wipe kit comprising:
(a) a propellantless finger actuated mechanical pump dispenser containing a propellant-free foamable aqueous composition according to claim 15, capable of forming a stable foam on dispensing; and
(b) a disposable substrate for receiving the stable foam.

22. A vaginal or hemorrhoidal foam wipe kit comprising:
(a) a propellantless finger actuated mechanical pump dispenser containing a propellant-free foamable aqueous composition according to claim 17, capable of forming a stable foam on dispensing; and
(b) a disposable substrate for receiving the stable foam.

23. A propellant-free foamable aqueous composition comprising:
(a) water;
(b) surfactant in an amount from about 2% to about 35% by weight, based on the total weight of the aqueous composition, wherein the surfactant consists essentially of a combination of polysorbate 20, triethanolamine-cocoyl glutamate and disodium cocoamphodiacetate; and
(c) foam stabilizing agent in an amount from about 0.10% to about 5% by weight, based on the total weight of the aqueous composition, wherein the foam stabilizing agent consists essentially of a combination of glycerine, xanthan gum and polyethylene glycol (23 oxyethylene) or a combination of propylene glycol and xanthan gum;
wherein the propellant-free foamable aqueous composition is capable of forming a stable foam when dispensed from a propellantless finger actuated mechanical pump dispenser, wherein the stable foam maintains the integrity of a disposable substrate to which it is applied and wherein the stable foam is suitable for application to the vaginal or anal area.

24. The propellant-free foamable aqueous composition according to claim 23 further comprising a medicament.

25. The propellant-free foamable aqueous composition according to claim 24, wherein the medicament is selected from the group consisting of pramoxine HCl, phenylephrine HCl, ephedrine sulfate, dibucaine HCl and combinations thereof.

\* \* \* \* \*